United States Patent [19]

Jorgenson et al.

[11] Patent Number: 5,289,140
[45] Date of Patent: Feb. 22, 1994

[54] CONSISTENT DIAGNOSTIC TEST METHOD USING MICROWAVES

[75] Inventors: Finn Jorgenson, Santa Barbara; Bent B. Vaboe, Carpinteria, both of Calif.

[73] Assignee: Dako Japan Co., Ltd., Kyoto, Japan

[21] Appl. No.: 745,688

[22] Filed: Aug. 16, 1991

[51] Int. Cl.$^5$ .................. H03B 1/00; H05B 6/80; G01N 22/00; G01N 33/48
[52] U.S. Cl. ................................. 331/74; 73/863.11
[58] Field of Search ................ 331/96, 56, 68, 74, 331/78; 219/10.55 B; 73/863.11

[56] References Cited

U.S. PATENT DOCUMENTS

| | | | |
|---|---|---|---|
| 2,895,828 | 7/1959 | Kamide | 219/10.55 B |
| 3,867,607 | 2/1975 | Ohtani | 219/10.55 B |
| 4,314,128 | 2/1982 | Chitre | 219/10.55 B |

Primary Examiner—David Mis
Attorney, Agent, or Firm—Poms, Smith, Lande & Rose

[57] ABSTRACT

Use of microwave equipment for fast food preparation and for speeding up chemical reactions e.g. in diagnostic testing is wellknown. However in all such uses the known equipment provides a very uneven heating effect, thereby limiting the value of the method. The present patent application describes an improved type of microwave equipment, in which an even effect is obtained by the use of a combination of microwaves of different wavelengths. The equipment according to the invention includes one or more microwave sources, controlled individually or jointly, emitting microwaves of a two or more wavelengths, e.g. in the form of distinct single wavelengths, White Noise, Square Waves.

15 Claims, 1 Drawing Sheet

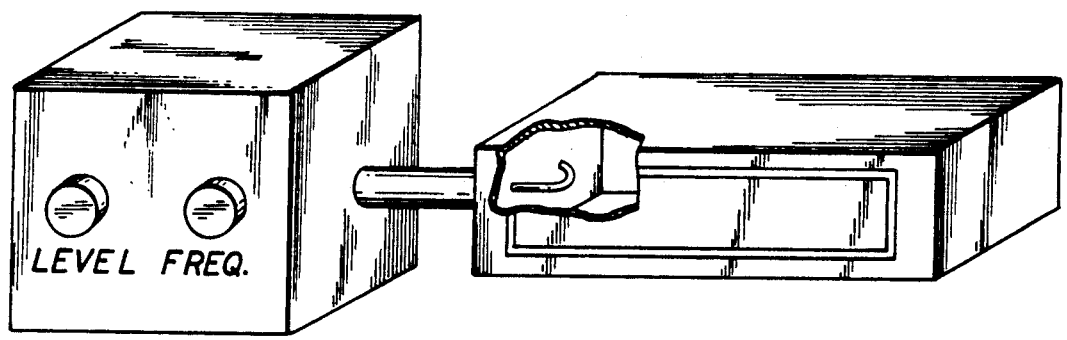
FIG. 1
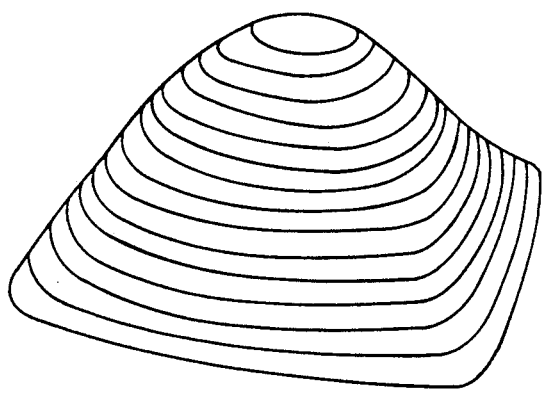
FIG. 2
PRIOR ART
FIG. 3
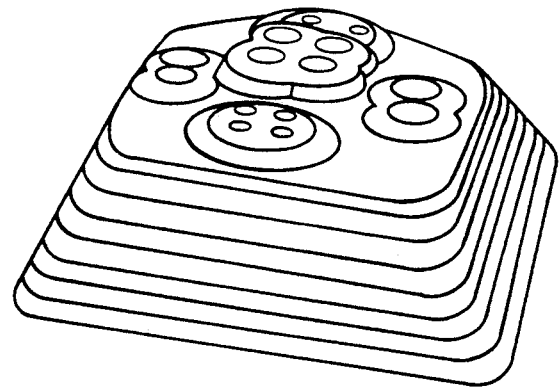

CONSISTENT DIAGNOSTIC TEST METHOD USING MICROWAVES

It is well-known that microwaves can be used for increasing chemical reaction rates and thereby shortening the time needed for reaching reaction equilibria. This fact is of importance in connection with diagnostic test procedures, and microwave ovens are already in use for reducing the time required for certain diagnostic tests, especially when it is essential to obtain the test results as fast as possible, e.g. in connection with surgical operations.

Microwave ovens are also in common use for food preparation in professional and private kitchens, and present here also the drawback associated with uneven effects from the center of the oven towards the boundaries.

In immunohistochemical test procedures the specimen to be tested is placed on a thin glass slide on which all the test reactions take place. The test procedure comprises several process steps, including pretreatment of the specimen e.g. with alcohol or acetone often followed by an enzymatic pretreatment with a proteolytic enzyme; the specimen is then subjected to a solution containing a specific antibody, which will react by coupling to the corresponding antigenic sites on the specimen; secondary antibodies carrying visualization agents may then be added to react with the primary antibody molecules tied to the antigens. The visualization agents may be a radioactive label, a fluorescent compound or an enzyme, which in a subsequent process step may give rise to a color reaction with other reagents added.

To achieve the desired results a strict protocol must be followed when performing the test allowing a certain specified reaction time for each of the process steps involved. The total time required for carrying out a test is usually in the range of 30 minutes to several hours, depending on the test system used; some test systems are developed especially for short reaction times by using high concentration of reagents and by other means, thereby reducing reaction times to the range of typically 15-30 minutes.

It is well-known that the total reaction time for the above procedures may be reduced by exposing the specimen to microwave radiation during some or all of the process steps included in the test.

When using the microwave technique for diagnostic test procedures a special protocol specifying the exact reaction times etc must be followed for each particular test. The procedure to be followed is very similar to the procedure used without microwaves, except that for some process steps the microscopy glass slide containing the specimen and the relevant reagents is placed in the microwave chamber or microwave oven for the specified time periods, usually a few minutes.

The use of microwave techniques is thus in principle very simple and requires no special skills other than the skills required for performing a standard diagnostic test without the use of microwaves. Given the considerable interest in shortening the time required for analysis it is therefore surprising that the technique has failed to gain acceptance for general use.

The equipment—microwave ovens—used today for applying microwave radiation to test specimens in connection with diagnostic procedures, gennerally have the serious drawback of giving a very uneven radiation intensity throughout the radiation chamber. The purpose of using microwave radiation is to reduce the reaction time required, but if radiation intensity is insufficient the chemical reaction will not proceed to the desired extent in the shortened time allotted to each process step; and if the radiation intensity is uneven in the area where the specimens are placed there will be a great uncertainty as to the extend to which the reaction has taken place, and thus an extra uncertainty is imposed on the test results.

Previous attempts to equalize the radiation intensity throughout the microwave radiation chamber include the introduction of a rotating table within the chamber, on which the specimens are placed during their exposure to radiation. This method however still fails to assure a satisfactory consistency in test results and its application makes the equipment unnecesarily complicated mechanically, especially as a high rotation speed seems to be necessary for obtaining any equilization effect with exposure times of only a few minutes.

It has now surprisingly been found that a very substantial evening out of the radiation intensity can be obtained without the use of mechanical means. According to the present invention the radiation intensity can be evened out throughout a large part of the radiation chamber by modifying the source of radiation compared to the presently used microwave equipment.

The present microwave equipment available on the market is to our knowledge limited to equipment having a microwave source emitting microwaves of a wavelength corresponding to the dimensions of the radiation chamber. As the result a standing wave is established, with its intensity being at maximum right in the middle of the chamber and declining towards the walls, where the intensity will be zero.

BRIEF DESCRIPTION OF THE DRAWINGS

FIG. 1

The present invention comprises an improved microwave equipment, in which the microwave source emits waves of more than one wavelength.

FIGS. 2-3

Thereby the distribution of microwave intensity will be much improved, because the waves of different wavelength will have their maximum intensities at different locations in the radiation chamber.

In a preferred embodiment of the invention the microwave source or sources emits waves of two different wave lengths. Thereby a certain equilization of radiation intensity is obtained with a rather simple and inexpensive radiation source.

In a preferred embodiment of the invention the microwave source comprises two separate microwave sources, which in some cases may may be more economical than having them combined. Preferably the two sources are controllable individually, whereby it becomes possible to further equalize the distribution of radiation intensity throughout the chamber by adjusting the intensity of each microwave of different wavelength in an optimal way.

In a further preferred embodiment of the invention the microwave source or sources emits waves with a distinct number of wavelengths, e.g. three or four corresponding wavelengths. Thereby the pattern of wave intensity throughout the radiation chamber may be optimized.

In a preferred embodiment of the invention the microwave source comprises two or more separate microwave sources, which in some cases may be more economical than having them combined. Preferably the individual sources are controllable individually, whereby it becomes possible to further equalize the distribution of radiation intensity throughout the chamber by adjusting the intensity of each microwave of different wavelength in an optimal way.

A further preferred embodiment of the invention comprise a microwave equipment, in which the microwave source emits waves with a broad spectrum of wavelengths, e.g. in the form of "white noise". Thereby the desired equalization of radiation intensity is obtained with a single, economical wave source.

A further preferred embodiment of the invention comprise a microwave equipment, in which the microwave source emits square waves with a spectrum of wavelengths including the 1st, 3rd, 5th etc. harmonics.

The microwave equipment according to the above may preferably be built into suitable enclosures to eliminate radio frequency interference; said enclosures may further include other known features to make the equipment easy to use for routine purposes both in professional environment such as in the clinical laboratory and in private use e.g. for food preparation in professional or private kitchens.

We claim:

1. A method for immunohistochemical testing comprising the steps of:
   placing a sample to be tested on a sample slide;
   treating the sample;
   placing the sample and slide in a microwave cavity;
   uniformly energizing the microwave cavity using microwave energy source means including at least three different wavelengths; and
   energizing the cavity for a predetermined specified reaction time,
   whereby samples are energized consistently with the proper level of microwave energy despite the variations in heating normally found in microwave heating cavities.

2. A method as defined in claim 1, wherein said step of uniformly energizing the microwave cavity includes the application of microwave energy from a substantially square wave source.

3. A method as defined in claim 1, wherein said step of uniformly energizing the microwave cavity includes the application of microwave energy from a substantially white noise source.

4. A method as defined in claim 1, including the additional step of removing the slide from the microwave cavity to review the visualization agents resulting from the process steps.

5. A method as defined in claim 1, wherein said step of uniformly energizing the microwave cavity includes applying the microwave energy to the cavity through a single radiating means coupled to the cavity.

6. A method for immunohistochemical testing comprising the steps of:
   placing a sample to be tested in a sample slide;
   treating the sample;
   placing the sample and slide on a small shelf in a microwave cavity;
   uniformly energizing the microwave cavity using microwave energy source means including at least three different wavelengths; and
   energizing the cavity for a predetermined specified reaction time,
   whereby samples are energized consistently with the proper level of microwave energy despite the variations in heating normally encountered throughout microwave heating cavities.

7. A method as defined in claim 6, wherein said step of uniformly energizing the microwave cavity includes the application of microwave energy from a substantially square wave source.

8. A method as defined in claim 6, wherein said step of uniformly energizing the microwave cavity includes the application of microwave energy from a substantially white noise source.

9. A method as defined in claim 6, including the additional step of removing the slide from the microwave cavity to review the visualization agents resulting from the process steps.

10. A method as defined in claim 6, wherein said step of uniformly energizing the microwave cavity includes applying the microwave energy to the cavity through a single radiating means coupled to the cavity.

11. A method as defined in claim 6, wherein the method includes the step of placing the sample on a microscopy glass slide.

12. Improved microwave equipment comprising:
    a microwave source emitting waves of more than one frequency; and
    means for supporting an immunohistochemical sample for uniform irradiation by said source.

13. Microwave equipment as defined in claim 12, further comprising a microwave cavity coupled to said microwave source.

14. Microwave equipment as defined in claim 13, wherein said microwave cavity is provided with a door, and a small internal shelf is provided behind said door.

15. Microwave equipment as defined in claim 14, wherein a glass slide carrying said sample is mounted on said shelf.

* * * * *